United States Patent [19]

Sutton et al.

[11] Patent Number: 4,997,772
[45] Date of Patent: Mar. 5, 1991

[54] WATER-INSOLUBLE PARTICLE AND IMMUNOREACTIVE REAGENT, ANALYTICAL ELEMENTS AND METHODS OF USE

[75] Inventors: Richard C. Sutton; Susan B. Littlehale; Susan J. Danielson, all of Rochester, N.Y.

[73] Assignee: Eastman Kodak Company, Rochester, N.Y.

[21] Appl. No.: 98,583

[22] Filed: Sep. 18, 1987

[51] Int. Cl.$^5$ .......................................... G01N 33/546
[52] U.S. Cl. .................................... 436/533; 436/534; 435/7.34; 435/36; 435/5; 422/56; 523/201; 525/902
[58] Field of Search ..................... 435/5, 7, 36; 422/55–57; 436/518, 531–534; 523/201; 525/902

[56] References Cited

U.S. PATENT DOCUMENTS

| | | | |
|---|---|---|---|
| 2,451,022 | 10/1948 | Dohrmann | 167/13 |
| 3,992,158 | 11/1976 | Przbylowicz et al. | 422/57 |
| 4,143,203 | 3/1979 | Rigopulos et al. | 428/407 |
| 4,210,723 | 7/1980 | Dorman et al. | 435/180 |
| 4,259,313 | 3/1981 | Frank et al. | 424/8 |
| 4,283,382 | 8/1981 | Frank et al. | 424/8 |
| 4,342,739 | 8/1982 | Kakimi et al. | 424/1 |
| 4,401,765 | 8/1983 | Craig et al. | 436/533 |
| 4,413,070 | 11/1983 | Rembaum | 523/223 |
| 4,415,700 | 11/1983 | Batz et al. | 524/548 |
| 4,419,453 | 12/1983 | Dorman et al. | 436/534 |
| 4,480,042 | 10/1984 | Craig et al. | 436/533 |
| 4,486,530 | 12/1984 | David et al. | 435/7 |
| 4,563,431 | 1/1986 | Pauly et al. | 436/533 |
| 4,581,337 | 4/1986 | Frey et al. | 436/533 |
| 4,618,576 | 10/1986 | Rosenstein et al. | 435/7 |
| 4,703,018 | 10/1987 | Craig et al. | 436/518 |
| 4,710,525 | 12/1987 | Kraemer et al. | 523/201 |
| 4,847,199 | 7/1989 | Snyder et al. | 435/7 X |

FOREIGN PATENT DOCUMENTS

| | | |
|---|---|---|
| 0174195 | 3/1986 | European Pat. Off. |
| 0227173 | 7/1987 | European Pat. Off. |
| 0256500 | 2/1988 | European Pat. Off. |

Primary Examiner—Robert J. Warden
Assistant Examiner—Jeffrey R. Snay
Attorney, Agent, or Firm—J. Lanny Tucker

[57] ABSTRACT

A water-insoluble polymeric particle has an inner core comprising a detectable tracer material distributed in a first polymer for which the tracer material has a high affinity. This first polymer has a glass transition temperature ($Tg_1$) less than about 100° C. The particle also has an outer shell comprising a second polymer for which the tracer material has substantially less affinity relative to said first polymer. This second polymer has a glass transition temperature ($Tg_2$) which is greater than or equal to the term [$Tg_1 - 10°$ C.]. It also contains groups which are either reactive with free amino or sulfhydryl groups of an immunoreactive species or which can be activated for reaction with such groups. Such a species can be covalently attached to this particle to form an immunoreactive reagent which is useful in analytical elements and various analytical methods including immunological methods, for example, agglutination assays.

23 Claims, No Drawings

WATER-INSOLUBLE PARTICLE AND IMMUNOREACTIVE REAGENT, ANALYTICAL ELEMENTS AND METHODS OF USE

FIELD OF THE INVENTION

This invention relates to a core/shell polymer particle containing a detectable tracer material in the core only. It also relates to an immunoreactive reagent and the use of that reagent in analytical elements and methods.

BACKGROUND OF THE INVENTION

Biologically active polypeptides or proteins which are attached to insoluble carrier materials, such as polymeric particles, have been used in a variety of ways. For example, the diagnosis of pathological or other conditions in human beings and animals is often carried out using immunological principles for the detection of an immunologically reactive species, for example antibodies or an antigen, in the body fluids of the person or animal. An antigen is generally known as a foreign substance, such as a drug, hapten, toxin, lectin, glycoprotein, polysaccharide, glycolipid, polypeptide or protein which, when introduced into the body, causes the production of certain soluble proteins known as antibodies.

Other proteins (such as enzymes or avidin) or biotin, have been covalently linked to various carrier materials for use in affinity chromatography, enzymatic reactions, analytical procedures, specific binding reactions and immunoassays. Among useful carrier materials are sheep and human erythrocytes, bacterial cells, latex particles, resinous particles and finely divided diazotized amino cellulose. For example, carrier particles prepared from sparingly water-soluble monomers (such as epoxy group-containing monomers) in the absence of emulsifiers are described in U.S. Pat. No. 4,15,700 (issued Nov. 15, 1983 to Batz et al).

The antigen-antibody reaction is the basis or all immunological test methods. The normal body response to a foreign substance has led to the development of a number of techniques which are used to diagnose various diseases, disorders and physiological conditions. Other specific binding reactions can occur between a ligand and corresponding receptor compounds. For example, avidin or a derivative thereof specifically reacts with biotin or a derivative thereof. Other specific binding reactions occur between enzymes and their substrate analogs, inhibitors or cofactors, lectins and sugars (including mono-, oligo- and polysaccharides and glycoproteins), nucleic acids and complementary base sequences, histones and binding proteins, and hormones and their receptors. In a general sense, one component of the reaction can be defined as the ligand while the corresponding component which reacts with it is considered the receptor.

In vitro tests for the presence of a suspected protein (for example, an antigen or antibody) in a biological sample are carried out by adding the immunological counterpart to the biological sample. If the suspected substance is present, the resulting antigen-antibody reaction can be demonstrated by precipitation of the antigen-antibody complex. This reaction complex is generally difficult to detect visually. For this reason, either antibodies or antigens are often bound to insoluble particles, for example polymer latex particles, so that when the complex is formed, it is readily detectable from the resulting agglutination either by observing the presence of clumping or by a detectable tracer associated with the particles. Agglutination is characterized by the clumping of particles from a suspension of particles. Further details of known agglutination methods are provided in U.S. Pat. No. 4,419,453 (issued Dec. 6, 1983 to Dorman et al) and U.S. Pat. No. 4,459,361 (issued July 10, 1984 to Gefter).

Immunoreactive reagents are described in U.S. Pat. No. 4,259,313 (issued Mar. 31, 1981 to Frank et al). These reagents are composed of a polymer or mixture of polymers in particulate form having distributed throughout the particles a fluorescent rare earth chelate which renders the reagents detectable using suitable equipment. Attached to the particles are molecules of an immunological species such as an antibody or antigen. The resulting reagent can be used in immunoassays. However, fluorometric equipment is required with these reagents. There are many instances where such equipment is not available or practical. For example, it would be useful to have immunoreactive reagents which can be detected readily by a user without the need for detection equipment either in a consumer's home or in a doctor's office. Such reagents would desirably be detectable within a few minutes visually with the unaided eye.

As a result, it has been proposed to incorporate various dyes or color-forming materials within such reagents by dispersing them within the polymeric particle as described, for example, in E.P. Publication 227,173. While this makes the reagents readily detectable, surprisingly it has been found that dye molecules on the surface of the particles often interfere with immunological reactions, such as those required for agglutination assays. Other materials on the surface of such particles, such as surfactants or stabilizers can also similarly interfere with the reactions.

U.S. Pat. No. 4,401,765 (issued Aug. 30, 1983 to Craig et al) describes a reagent which is a core/shell polymer having an immunological species attached thereto. These reagents contain no tracer material, and are detected in the assay through light scattering techniques which require sophisticated equipment that would be available only in a clinical chemistry laboratory. Even the simplest technique involving the measurement of turbidity requires the use of a spectrophotometer (see Col. 4, lines 1–56). These techniques clearly would not be useful for assays which are to be carried out at home, in doctors' offices and other places where equipment is limited or impractical. Hence, there is a need for a readily detectable immunoreactive reagent which can be easily detected without complicated equipment and procedures and which avoids the interference caused by materials on the surface of particles.

SUMMARY OF THE INVENTION

The problems noted above with known reagents have been overcome with an immunoreactive reagent comprising:

(a) a water-insoluble polymeric particle having:

an inner core comprising a detectable tracer distributed within a first polymer for which the tracer has a high affinity and which has a glass transition temperature ($T_{g1}$) less than about 100° C., the first polymer being derived from one or more ethylenically unsaturated polymerizable monomers, and an outer shell comprising a second polymer for which the tracer has substantially less affinity relative to the first polymer, the second polymer having a glass transition temperature ($T_{g2}$) greater than or equal to the term [$T_{g1}-10°$ C.], and which is derived from one or more ethylenically unsaturated polymerizable monomers, at least one of which monomers has reactive groups which are either directly or indirectly reactive with free amino or sulfhydryl groups of an immunoreactive species, the particle having substantially none of the tracer within the outer shell or on its outer surface, and the particle being covalently attached through the reactive groups on the outer surface to (b) an immunoreactive species which is capable of participating in an immunological reaction with a compound of biological interest.

This reagent is prepared using a water-insoluble polymeric particle having:

an inner core comprising a detectable tracer distributed within a first polymer for which the tracer has a high affinity and which has a glass transition temperature ($T_{g1}$) less than 100° C., the first polymer being derived from one or more ethylenically unsaturated polymerizable monomers, and an outer shell comprising a second polymer for which the tracer has substantially less affinity relative to the first polymer, the second polymer having a glass transition temperature ($T_{g2}$) greater than or equal to the term [$T_{g1}-10°$ C.], and which is derived from one or more ethylenically unsaturated polymerizable monomers, at least one of which monomers has reactive groups which are either directly or indirectly reactive with free amino or sulfhydryl groups of an immunoreactive species, the particle having substantially none of the tracer within the outer shell or on its outer surface.

Aqueous suspensions of the polymeric particles or immunoreactive reagents described above are also the subject of this invention.

This invention also provides an analytical element comprising an absorbent carrier material having one or more zones, and containing in one or more of the zones the immunoreactive reagent described above.

A method for the determination of a compound of biological interest in an aqueous liquid comprises:

A. contacting the liquid with the immunoreactive reagent described above, so as to form an insoluble reaction product of the biological compound and the immunoreactive species, and B. determining the amount of tracer either in the reaction product or the unreacted materials.

The present invention provides reagents which can be used in a wide variety of immunological techniques to provide highly sensitive assays. The water-insoluble polymeric particles used to prepare the reagents have readily available reactive groups on the outer surface which either directly react with immunoreactive species which have free amine or sulfhydryl groups, or which are indirectly reactive with the groups through activation or linking moieties. In all cases, the species is attached to the particles covalently.

The reagents are readily detectable without the use of sophisticated spectrophotometric or light scattering equipment. This advantage is provided by the use of a tracer material within the particles which is readily detected with the unaided eye or with inexpensive equipment. In a preferred embodiment, the tracer is a dye which is readily visible to the unaided eye. This renders the assay of the present invention suitable for a consumer product which could be purchased and used by the average consumer with little technical expertise or equipment. It could also be used in doctors' offices where sophisticated equipment may be unavailable.

In an attempt to make dyed agglutination reagents, it was unexpectedly found that residual dye on the outer surface of the particles interfered with the reaction of antibody with antigen. The reagents of the present invention, however, are prepared having tracer material within the particles, but they do not exhibit this problem. The problem of interference is avoided by using particles that are known in the art as "core/shell" particles. Such particles comprise one polymer in the core and a second one in the shell. In the present invention, the core polymer is such that the tracer has a high affinity therefore, whereas the tracer has substantially less affinity for the shell polymer relative to the core polymer. In other words, the tracer is solubilized to such a greater degree in the core polymer than in the shell polymer that substantially all of the tracer is in the core. It was surprising that core/shell polymers could be designed that would readily accept tracer materials in the core only while the shell is essentially free of tracer material. The features of the polymers which provide this advantage are described in more detail below.

DETAILED DESCRIPTION OF THE INVENTION

The present invention provides a core/shell polymeric particle and a reagent prepared therefrom for use in analytical elements and methods. The method of use can provide an analytical determination very quickly. This permits the assay to be performed in a doctor's office or at home by a consumer who would like immediate diagnostic results. The test can be used to detect the presence or absence or amount of an immunoreactive species in an aqueous liquid, for example a biological sample.

An immunoreactive species is defined herein as any biological or chemical compound which has one or more sites for complexing with a corresponding specific binding receptor molecule. For example, the species could be an immunological species which is (1) any substance which, when presented to an immunocompetent host, will result in the production of a specific antibody capable of binding with that substance, or (2) the antibody so produced, which species participates in an antigen-antibody reaction in the use thereof. Representative immunological species include primary amines, amino acids, peptides, proteins, lipoproteins, glycoproteins, drugs, steroids, lipids, nucleic acids, hormones, vitamins, polysaccharides, glycolipids, alkaloids, organisms (bacteria, protozoa, fungi, viruses, rickettsia and the like) and components, thereof, blood substances, tissue and organ antigens and other materials known to one skilled in the art (see for example, U.S. Pat. No. 4,181,636). In some instances, the immunological species is an antibody which is directed against a drug, hormone, antibiotic or other compound having antigenic properties. Alternatively, the immunological species can be an antigenic material. In still another embodiment, the immunological species is an antibody which is directed against another antibody (that is, an anti-antibody). Both monoclonal and polyclonal antibodies can be used, and they can be whole molecules or various fragments thereof, as long as they have at least one reactive amine or sulfhydryl group which can be directly or indirectly reacted with the pendant reactive groups on the surface of the outer shell of the polymeric particles of this invention.

The present invention is not limited to immunological species. The immunoreactive species attached to the particles can be enzymes, proteins or other biological compounds which are not immunological, but which have one or more sites for complexing with a corresponding receptor molecule.

The immunoreactive species can be directly or indirectly attached to the particles with or without activation or through linking moieties.

By "direct" attachment is meant herein that the immunoreactive species reacts directly with the reactive groups on the outside of the particles without any activation or linking moieties. In contrast, "indirect" attachment is used to define reaction of the immunoreactive species after the reactive groups have been activated to make them directly reactive (for example, activation of carboxyl groups using carbodiimides), or the use of linking moieties attached either to the species or to the particles (for example, see U.S. Pat. No. 4,581,337, issued Apr. 8, 1986 to Frey et al). In some cases, certain linking moieties can be used to attach the immunoreactive species even if the reactive groups on the particles are capable of "direct" attachment.

The immunoreactive species which is part of the immunoreactive reagent, then, is a receptor molecule for the immunoreactive species to be detected, and the converse is true.

In certain embodiments, the immunological species is an enzyme attached to the polymeric particle. Enzymes which can be attached in this manner include those which have reactive amine groups which can be reacted with the active groups on the polymer particles. Representative enzymes include aspartate aminotransaminase, alanine aminotransaminase, lactate dehydrogenase, creatine phosphokinase, gamma glutamyl transferase, alkaline phosphatase, and prostatic acid phosphatase. Methods of making such reagents are well known in the art.

The water-insoluble reagent of the present invention is prepared by attaching the immunological species described above to a water-insoluble polymeric particle of specific composition. These particle are prepared from the ethylenically unsaturated polymerizable monomers described below such that there are pendant reactive groups. Such groups are free and capable of direct or indirect reaction with the amine or sulhydryl groups of an immunoreactive species as described above.

The polymeric particles are generally water-insoluble latex particles having a particle size greater than about 0.01 micrometers, preferably in the range of from about 0.01 to about 5 micrometers, and more preferably from about 0.3 to about 3 micrometers.

The particles of this invention have an inner core of a first polymer and a shell of a second polymer, in a similar arrangement as described in U.S. Pat. No. 4,401,765 (noted above). Generally, the core of the particles is composed of a first polymer for which the tracer (described below) has high affinity. That is, the tracer material and first polymer are matched such that the tracer is readily solubilized or dissolved within the polymer. Generally, the tracer material (for example a colorimetric or fluorescent compound, or dye forming compound) is highly hydrophobic and therefore, the first polymer must be hydrophobic as well. This first polymer is derived from ethylenically unsaturated polymerizable monomers having one or more ethylenically unsaturated polymerizable moieties.

Although any core/shell polymeric particle having a tracer material in the core only and reactive groups on the outer surface capable of reaction with an immunoreactive species is contemplated as a new composition of this invention, the following formulae (I) and (II) describe preferred compositions. These compositions are preferred for their ability to incorporate tracer materials selectively into the core of the particles by the relatively simple imbibition techniques illustrated herein and discussed in detail in U.S. Pat. No. 4,199,363 (issued Apr. 22, 1980 to Chen). The tracers preferred for use in these preferred compositions are aromatic dyes (such as the most preferred azo dyes) which are solubilized primarily by the hydrophobic (for example, aromatic) groups in the core polymer. In some instances, solubilization of the tracer material in the core polymer is facilitated by hydrogen bonding.

Useful first polymers have a glass transition temperature (identified herein as $T_{g1}$) less than about 100° C., and preferably from about −25° to about 95° C., in order to facilitate solubilization and immobilization of the tracer material in the core polymer. This $T_{g1}$ is a calculated value determined using the following equation [with the glass transition temperature values in °K. (Kelvin) which can be readily converted to °C.]:

$$\frac{1}{T_{g1}} = \left[\frac{1}{(T_g)_{m1}}\right]x_1 + \left[\frac{1}{(T_g)_{m2}}\right]x_2 + \ldots + \left[\frac{1}{(T_g)_{mn}}\right]x_n$$

wherein m1, m2, ... mn represent the individual monomers from which the first polymer is derived and identify the Tg (°K.) of the homopolymer prepared from each individual monomer, $x_1, x_2, \ldots x_n$ represent the weight fractions of the monomers used to prepare the first polymer, and n represents the number of monomers used to prepare the first polymer.

Preferred first polymers are represented by the formula (I):

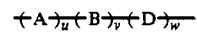

wherein —A— represents recurring units derived from one or more hydrophobic ethylenically unsaturated monomers which provide water insolubility to the particles, —B— represents recurring units derived from one or more ethylenically unsaturated monomers whose homopolymers have a glass transition temperature (that is Tg) less than about 55° C., and —D— represents recurring units derived from one or more ethylenically unsaturated monomers which are different than those represented by —A— or —B— which, in the amounts used, do not deleteriously reduce water insolubility of the particles or solubilization of the tracer material in the core.

In the structural formula above, u is from about 30 to about 95 mole percent, v is from 5 to about 50 mole percent, and w is from 0 to 20 mole percent. Preferably, u is from about 55 to about 95 mole percent, v is from about 5 to about 35 mole percent, and w is from 0 to about 10 mole percent.

Monomers from which the —A— recurring units are derived are hydrophobic and form homopolymers that are insoluble in water. Preferably, these monomers have aromatic groups. Representative hydrophobic monomers include, but are not limited to, styrene and styrene derivatives (for example, 4-vinyltoluene, 2,5-dimethylstyrene, 4-t-butylstyrene, 2-chlorostyrene and others known in the art), acrylic and methacrylic acid esters and amides (for example, n-butyl acrylate, propyl methacrylate, methyl acrylate, methyl methacrylate, ethyl methacrylate, 2-ethylhexyl methacrylate, N-phenylacrylamide and others known in the art), acrylonitrile and vinyl acetate.

The polymer useful in this invention in making the core can be crosslinked, if desired, in any suitable fashion. One method is to incorporate a small amount, that is up to about 10 mole percent, and preferably from about 0.3 to about 5 mole percent, of a monomer having two or more ethylenically unsaturated polymerizable groups. These monomers are included among the hydrophobic monomers from which A is derived. Representative monomers are described in *Research Disclosure*, publication 19551, July, 1980, page 304, and include for example, divinylbenzene, ethylene dimethacrylate, N,N'-methylenebisacrylamide 2,2-dimethyl-1,3-propylene diacrylate, allyl acrylate, ethylidyne trimethacrylate and ethylene diacrylate. Crosslinking with such monomers, however, reduces the swellability of the core caused by the organic solvent used in the preferred imbibing techniques. Therefore, crosslinking is generally limited to small amounts as required to impart water-insolubility of the core.

Preferred monomers from which the —A— recurring units are derived are vinyl aromatic monomers, especially styrene and styrene derivatives.

The monomers from which the —B— recurring units are derived include those which when polymerized, form homopolymers which have a Tg of less than about 55° C. Representative monomers include, but are not limited to, those having active methylene groups [2-acetoacetoxyethyl methacrylate, ethyl acryloylacetate, 6-vinylphenyl-2,4-hexanedione, N-(2-acetoacetoxyethyl)acrylamide, and others known in the art, for example, as described in U.S. Pat. Nos. 3,459,790, 3,904,418, 3,929,482, 3,939,130 and 4,247,673], and monomers having amino, hydroxy, ester, amide and ketone moieties (such as butyl acrylate, 2-ethylhexyl acrylate, 2-aminoethyl acrylate, 2-hydroxyethyl acrylate, 2-hydroxyethyl methacrylate, 2,3-dihydroxypropyl acrylate, benzyl acrylate, butyl acrylate, ethyl acrylate, cyclohexyl acrylate and others known in the art).

It is evident that some of the monomers have more than one of the desired requirements, for example, providing $Tg_1$ and hydrophobicity, thus there is some overlap among the monomers for the —A— and —B— units. However, there are some monomers which are useful for either —A— or —B— units alone.

Preferred monomers from which —B— units are derived include 2-acetoacetoxyethyl methacrylate, 2-ethoxyethyl acrylate, butyl acrylate, cyclohexyl acrylate and benzyl acrylate.

Monomers from which the —D— recurring units are derived include any monomer other than those defined for the —A— and —B— units above. Preferably, these monomers are more polar than the —A— or —B— monomers. Representative monomers include, but are not limited to, anionic monomers such as sodium 2-acrylamido-2-methylpropanesulfonate, acrylic acid, methacrylic acid, 2-carboxyethyl acrylate, styrene sulfonic acid, potassium salt and m and p-carboxymethylstyrene and other ethylenically unsaturated polymerizable sulfonates, carboxylates, sulfates and phosphonates.

Preferred D monomers are sodium 2-acrylamido-2-methylpropanesulfonate, acrylic acid, methacrylic acid, styrene sulfonic acid and m and p-carboxymethylstyrene.

Representative first polymers of which the core of the particles can be composed include the following materials (the $Tg_1$ values have been calculated for some of the polymers): poly(styrene-co-2-acetoacetoxyethyl methacrylate) (50:50, 70:30, 85:15 and 95:5 molar ratios, having $Tg_1$s of 27°, 47°, 69° and 91° C., respectively), poly(styrene-co-m and p-chloromethylstyrene-co-2-hydroxyethyl acrylate) (67:30:3 molar ratio), poly(styrene-co-n-butyl acrylate) (78.7:21.3 molar ratio, $Tg_1$ of 47° C.) and poly(styrene-co-benzyl acrylate)(90:10 molar ratio).

The shell of the particles of the present invention comprises a second polymer which provides reactive sites for covalent bonding of the immunoreactive species, and sufficient swellability in water-miscible organic solvents used in the preferred manner of imbibing tracer materials into the core of the particles without encouraging retention of the tracer material in the shell. Therefore, the shell polymer can have a minimal amount of —B— recurring units described above for the first polymer. That is, enough of those units can be used to impart swellability but not too much as to solubilize the tracer material. The shell may be sufficiently swellable without the incorporation of —B— units.

Generally, the second polymer has a $Tg_2$ which is equal to or greater than the term [$Tg_1$ less 10° C.]. $Tg_2$ is usually greater than $Tg_1$, but it can be equal to $Tg_1$, or as much as 10° C. less than $Tg_1$.

More specifically, preferred second polymers can be represented by the formula (II):

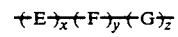

wherein —E— represents recurring units derived from one or more hydrophobic ethylenically unsaturated monomers, —F— represents recurring units derived from one or more ethylenically unsaturated monomers having the requisite reactive groups which will directly or indirectly react with the free amine or sulfhydryl groups of the immunoreactive species described herein, and —G— represents recurring units derived from one or more ethylenically unsaturated monomers which are different than those represented by —E— or —F—.

In formula (II), x is from 0 to about 99.9 mole percent, y is from about 0.1 to 100 mole percent, and z is from 0 to about 15 mole percent. Preferably, x is from about 45 to about 99 mole percent, y is from about 1 to about 50 mole percent, and z is from 0 to about 5 mole percent.

Monomers from which the —E— recurring units are derived, both in general and in preferred embodiments, are the same as those defined from which the —A— recurring units of formula (I) are derived.

The monomers from which the —F— recurring units are derived include, but are not limited to, monomers having an active halogen atom (such as vinyl chloroacetate, chloroalkylated vinyl aromatics, for example chloromethylstyrene, or chloroalkyl acrylic or methacrylic esters, for example chloroethyl methacrylate, 3-chloro-2-hydroxypropyl methacrylate, and 3-chloropropyl acrylate), monomers having one or more pendant carboxyl groups or their functional equivalents (such as acrylic acid, methacrylic acid, itaconic acid, maleic acid or their anhydrides), monomers containing epoxy groups (such as glycidyl acrylate, glycidyl methacrylate, vinyl glycidyl ether or methallyl glycidyl ether), monomers containing isocyanate groups (such as isocyanatoethyl acrylate, isocyanatoethyl methacrylate, or α, α-dimethylmetaisopropenylbenzyl isocyanate), amine-containing monomers [such as 2-aminoethyl methacrylate, and N-(3-aminopropyl)methacrylamide], monomers containing an aziridine group [such as vinylcarbamoyl aziridine, acryloyl aziridine, methacryloyl aziridine, N-acryloylaziridine and 2-(1-aziridinyl)ethyl acrylate], monomers containing aldehyde groups (such as vinyl benzaldehyde or acrolein), 2-substituted ethylcarbonyl containing monomers (such as 2-chloroethyl acrylate, 2-chloroethyl methacrylate, 2-methylsulfonyloxyethyl methacrylate and 2-p-tolylsulfonyloxyethyl acrylate) or monomers having pendant activated 2-substituted ethylsulfonyl or vinylsulfonyl groups [such as those described in U.S. Pat. No. 4,161,407 (issued July 17, 1979 to Campbell) and U.S. Pat. No. 4,548,870 (issued Oct. 22, 1985 to Ogawa et al)] and others known to one skilled in the art.

Preferred monomers from which —F— is derived include those having active halomethyl groups of 1 to 3 carbon atoms and the activated 2-substituted ethylsulfonyl and vinylsulfonyl monomers.

Preferred monomers having active halomethyl groups of 1 to 3 carbon atoms include chloromethylstyrene and bromomethylstyrene.

Preferred activated 2-substituted ethylsulfonyl and vinylsulfonyl monomers can be represented by the formula:

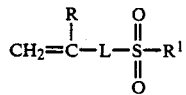

wherein R is hydrogen or substituted or unsubstituted alkyl (generally of 1 to 6 carbon atoms, such as methyl, ethyl, isopropyl or hexyl. Preferably, R is hydrogen or methyl.

$R^1$ is —CH=CHR$^2$ or —CH$_2$CH$_2$X wherein X is a leaving group which is displaced by a nucleophile or is eliminated in the form of HX by treatment with a base (such as halo, acetoxy, alkylsulfonyloxy such as methylsulfonyloxy, arylsulfonyloxy such as p-tolylsulfonyloxy, trialkylammonio, for example, a trimethylammonio salt or pyridinio salt). $R^2$ is hydrogen, substituted or unsubstituted alkyl (generally of 1 to 6 carbon atoms as defined for R), or substituted or unsubstituted aryl (generally of 6 to 12 nuclear carbon atoms, such as phenyl, naphthyl, xylyl or tolyl). Preferably, $R^1$ is —CH$_2$CH$_2$X. This group, which is an activated 2-substituted ethyl group, can be substituted with any group which does not impair the displacement of the leaving group X.

L is a linking group which can be a substituted or unsubstituted alkylene generally having 1 to 20 carbon and hetero atoms in the backbone. This definition of alkylene is meant to include alkylene groups interrupted or terminated with oxy, thio, —NR$^3$— [wherein R$^3$ is hydrogen, substituted or unsubstituted alkyl of 1 to 6 carbon atoms (such as methyl, chloromethyl or 2-hydroxyethyl) or substituted or unsubstituted aryl of 6 to 10 carbon atoms (such as phenyl, naphthyl or xylyl)], ester (—COO—), amide (—CONH—), urylene

sulfonyl (—SO$_2$—), carbonate, sulfonamide, azo, phosphono or other similar groups. Representative alkylene groups include methylene, ethylene, isobutylene, hexamethylene, carbonyloxyethyleneoxycarbonylethylene, methylenebis(iminocarbonyl)ethylene, carbonyloxydodecylenecarbonyloxyethylene, carbonyliminomethyleneiminocarbonyliminoethylene, carbonyliminomethyleneiminocarbonylethylene and other groups described or suggested by U.S. Pat. Nos. 4,161,107 and 4,548,870, noted above.

L can also be substituted or unsubstituted arylene generally having 6 to 12 nuclear carbon atoms. Representative arylene groups include phenylene, tolylene, naphthylene and others noted in the patents mentioned above. Also included in this definition of L are divalent groups which are combinations of one or more of each of the alkylene and arylene groups defined above (for example, arylenealkylene, alkylenearylenealkylene and others readily determined by one of ordinary skill in the art) as well as such combinations interrupted or terminated with one or more amide or ester groups (such as carbonyliminomethyleneiminocarbonyliminoethylene). Preferably, L is substituted or unsubstituted phenylenealkylene, phenylenealkylene substituted with one or more alkyl groups (as defined for R), alkoxy groups (generally of 1 to 6 carbon atoms, for example, methoxy, propoxy or butoxy) or halo groups, or carbonyliminomethyleneiminocarbonylethylene.

Representative useful monomers include m and p-(2-chloroethylsulfonylmethyl)styrene, m and p-[2-(p-tolylsulfonyloxy)ethylsulfonylmethyl]styrene, m and p-vinylsulfonylmethylstyrene, N-[m and p-(2-chloroethylsulfonylmethyl)phenyl]acrylamide, and N-[2-(2-chloroethylsulfonyl)ethylformamidomethyl]acrylamide. The first monomer is preferred.

Monomers from which the —G— recurring units are derived include monomers different than those from which —E— and —F— are derived. Specifically, the —G— recurring units are derived from monomers which impart aqueous dispersion stability to the particles or make retention of the tracer material in the shell unlikely. Representative monomers include, but are not limited to, anionic monomers such as those defined above for the —D— recurring units, other hydrophilic but nonionic monomers, such as 2-hydroxyethyl acrylate and 2-hydroxyethyl methacrylate and others known to one skilled in the art.

Preferred G monomers are acrylic acid, methacrylic acid, sodium 2-acrylamido-2-methylpropanesulfonate, m and p-carboxymethylstyrene and p-styrenesulfonic acid, potassium salt.

Representative second polymers of which the shell of the particles can be composed include the following (the $T_{g2}$ values have been determined for some of the materials): poly(m and p-chloromethylstyrene) ($T_{g2}$ of 82° C.), poly(styrene-co-m and p-chloromethylstyrene-co-2-hydroxyethyl acrylate (67:30:3 molar ratio), poly(styrene-co-m and p-chloroethylsulfonylmethylstyrene) (95.5:4.5 molar ratio, $T_{g2}$ of 105° C.), poly{styrene-co-N-[m and p-(2-chloroethylsulfonylmethyl)-phenyl]acrylamide} (99.3:0.7 molar ratio), poly(m and p-chloromethylstyrene-co-methacrylic acid)(95:5, 98:2 and 99.8:0.2 molar ratio, $T_{g2}$s of 85°, 83° and 82° C., respectively), poly(styrene-co-m and p-chloroethylsulfonylmethylstyrene-co-methacrylic acid)(93.5:4.5:2 molar ratio), poly{styrene-co-N-[m and p-(2-chloroethylsulfonylmethyl)phenyl]acrylamide-co-methacrylic acid}(97.3:0.7:2 molar ratio), poly(styrene-co-m and p-vinylbenzaldehyde)(95:5 molar ratio), poly(styrene-co-m and p-vinylbenzaldehyde-co-methacrylic acid)(93:5:2 molar ratio), poly(styrene-co-m and p-chloromethylstyrene)(70:30 molar ratio, $T_{g2}$ of 96° C.) and poly(styrene-co-methacrylic acid)(90:10 molar ratio, $T_{g2}$ of 113° C.).

The polymeric particles can be prepared using any suitable polymerization technique, including emulsion (including batch, semi continuous and continuous) and suspension polymerization techniques, graft copolymerization, and others known to one skilled in the polymer chemistry art. Emulsion polymerization is preferred as it can be used to provide particles without the use of surfactants or emulsifiers as described for example in U.S. Pat. No. 4,415,700 (noted above) and *Research Disclosure* publication 15963 (July, 1977). *Research Disclosure* is a publication available from Kenneth Mason Publications, Ltd., The Old Harbourmaster's, 8 North Street, Emsworth, Hampshire P010 7DD, England. Continuous emulsion polymerization is the most preferred technique, as described in the noted *Research Disclosure* publication. Other details of preparatory methods can be found in U.S. Pat. Nos. 4,161,407 and 4,548,870, noted above.

More particularly, staged emulsion polymerization can be used to provide a core-shell polymer composed of two different polymers. Emulsion polymerization of the core is carried to substantial completion by continuously adding reactants to a reaction vessel under standard conditions. Monomers and catalysts needed to make the shell polymer are then continuously added to the vessel containing the latex of the core polymer. In this manner, the shell has a definite known composition rather than being a mixture of core and shell monomers. Representative details of preparing the core-shell polymeric particles useful in this invention are provided in the Examples below.

The core polymer of the particle generally comprises from about 30 to about 80, and preferably from about 40 to about 70, weight percent of the particle.

The general procedure for preparing the reagent of this invention includes covalently attaching the immunological species to the particles using generally known reactions. With many pendant groups, for example the haloalkyl, 2-substituted activated ethylsulfonyl and vinylsulfonyl, the immunological species can be directly attached to the particles. Generally, the polymer particles are mixed with the immunological species in an aqueous buffered solution (pH generally from about 7 to about 10) and a concentration of from about 0.01 to about 40 weight percent polymer particles (preferably from about 0.01 to about 10 weight percent). The amount of immunological species is at a ratio of species to polymer of from about 0.1:1000 to about 1:10, and preferably from about 1:100 to about 1:10. Mixing is carried out at a temperature in the range of from about 5° to about 50° C., and preferably at from about 5° to about 40° C., for from about 0.5 to about 48 hours. Any suitable buffer can be used. The details of a representative preparatory procedure are illustrated in Example 1 below.

In some instances, the pendant reactive groups on the outer surface must be modified or activated in order to cause covalent attachment of the immunological species. For example, carboxyl groups must be activated using known carbodiimide chemistry, or using the carbamoylonium chemistry described in U.S. Ser. No. 098,429 entitled ATTACHMENT OF COMPOUNDS TO POLYMERIC PARTICLES USING CARBAMOYLONIUM COMPOUNDS, filed Sept. 18, 1987 by Sutton et al., now abandoned in favor of Continuation-in-part U.S. Ser. No. 286,097 (filed Dec. 19, 1988), now abandoned in favor of Continuation-in-Part U.S. Ser. No. 373,304 (filed June 29, 1989). The details of such activation procedures are known in the art, or available in the cited application, incorporated by reference herein.

In other instances, an epoxy group on the outer surface can be hydrolyzed to form a diol compound capable of reacting with cyanogen bromide which can act as a coupling agent for amine groups in the immunological species. Aldehydes can react directly with amines to form a Shiff's base which can be subsequently reduced to form a covalent link. Alternatively, the aldehyde can be oxidized to an acid and chemistry identified above for carboxyl groups can be used to form an amide linkage.

The polymeric particles used in this invention contain substantially no detectable tracer material within the shell or on its outer surface. A tracer is a material which is detectable with the unaided eye or by using appropriate equipment and techniques. This means that substantially all of the tracer is in the core of the particles.

Useful tracers include, but are not limited to, radioisotopes which emit gamma rays, fluorescent compounds or dyes, bioluminescent compounds, chemiluminescent compounds, chromogens such as dyes and dye-formers, and others known to one skilled in the art. Generally, they include any detectable material which can be suitably incorporated into the first polymer. This incorporation can occur by adding the tracer to the polymerizable monomers which are then polymerized. Alternatively, the core can be prepared and the tracer coated onto it, or incorporated internally in a suitable manner, for example, by imbibing the tracer into the core polymer using the procedure described, for example, in U.S. Pat. No. 4,199,363 (noted above) and U.S. Pat. No. 4,283,382 (issued Aug. 11, 1981 to Frank et al).

More preferably, the core/shell particles are prepared and a tracer material is imbibed into them using the techniques of the noted patents. Because the tracer has affinity for the core polymer and not the shell polymer, the tracer diffuses through the shell until it is in the core only. Representative details of such a procedure are described in Example 1 below.

Tracer materials which are preferred in the practice of this invention include, but are not limited to, colorimetric or fluorometric compounds.

In a preferred embodiment of this invention, the tracer material is an aromatic dye which is solubilized in the core polymer. Such dyes can be of any suitable color which is readily observed in an assay. Generally, they contain one or more aromatic moieties which render them soluble in organic solvents which are water-miscible. Such dyes are not considered water-soluble. Preferred aromatic dyes include azo dyes, such as Oil Red EGN (available from Aldrich Chemical Co., Milwaukee, Wisc.) and Kodak Oil Red O (available from Eastman Kodak Co., Rochester, N.Y.). Other useful dyes would be readily determined by a skilled chemist with routine experimentation by seeing which dyes have the desired organic solvent solubility and selective solubility in a particular core polymer.

The amount of tracer material in the core/shell particles will depend upon the particular material used and the amounts needed for suitable detection. When colored dyes are used, the amount is generally in the range of from about 0.1 to about 15 percent, based on particle weight.

When a dye is used as the tracer, a preferred method of incorporation into the particles comprises dissolving the dye in a suitable water-miscible organic solvent, adding the resulting solution incrementally to the polymer latex at a temperature in the range of 20° to 90° C., and removing the organic solvent in a suitable fashion. Of course, variations of this procedure, such as adding the polymeric latex to the dye solution as taught in U.S. Pat. No. 4,199,363 (noted above), can also be used. Filtration of the latex particles insures removal of particulate dye crystals. The ratio of organic solvent to water must be maintained at a level so as not to dissolve the polymer. Preferred solvents include acetonitrile, N,N-dimethylformamide, lower alcohols such as methanol and ethanol, tetrahydrofuran, ketones such as acetone, and 1-methyl-2-pyrrolidinone.

The core/shell particles containing tracer and the reagents prepared from them can be used, stored or provided in kits as aqueous suspensions.

The reagent of the present invention can be used in the determination (qualitative or quantitative measurement) of an analyte in aqueous liquids. This determination can be made by merely determining the presence or absence of the analyte, or by quantitatively determining the amount of analyte. Where the analyte is determinable by immunological methods, it is identified as a ligand herein. In particular, the invention can be used to assay biological fluids of animals, humans or plants, but preferably of humans. Such fluids include, but are not limited to, whole blood, plasma, sera, lymph, bile, urine, spinal fluid, seminal fluid, lacrimal fluid, vaginal secretions, sputum, perspiration and the like as well as stool specimens. It is also possible to assay fluid preparations of human or animal tissue such as skeletal muscle, heart, kidney, lungs, brains, bone marrow, skin and the like.

The present invention can be used to determine (that is, either qualitative or quantitative measurement) any of a wide variety of ligands which are reactive with the immunological species on the reagent of the invention. Such ligands include, but are not limited to, proteins, hormones, drugs, carbohydrates, plant lectins or lipopolysaccharides which have one or more sites for complexing with the immunological species of the reagent. For example, the reagent comprises antibodies directed against the ligand which may be a drug or hormone.

Alternatively, the ligand can be an antibody or antigen which has two or more sites for complexation with one or more immunological species, one of which is part of the reagent of this invention. In diagnostic assays described herein, the ligand can be Streptococcus A antigen, antigens from chlamydial or gonococcal organisms, HTLV antigens or antibodies (for example, HTLV-I or HTLV-II), HIV antigens or antibodies (for example, HIV-I or HIV-II), thyroid stimulating hormone, apolipoproteins, human chorionic gonadotropin, leutinizing hormone, carcinoembryonic antigen, hepatitis antigen, herpes viruses and other biological compounds.

The reagent can be used in a solution assay method in competitive binding immunoassays. By solution assay is meant that the reagents of this invention are used in liquid suspension in an immunoassay. Either bound (that is, complexed) or unbound (that is, uncomplexed) labeled materials can be determined. Physical separation of bound and unbound materials, if desired, can be carried out using any suitable separation technique. In using the analytical elements described below, either vertical or horizontal separation can be used.

In another embodiment, the reagent can be used in what are known in the art as immunometric assays, for example, "sandwich" assays. The details of such assays are provided in U.S. Pat. No. 4,486,530 (issued Dec. 4, 1984 to David et al). The reagent of the present invention is useful in such assays where the ligand to be determined has two or more epitopic sites for immunological reaction with two or more receptor molecules. The receptor molecules can be the same or different. One of the receptor molecules is identified herein as a first immunological species. A second immunological species is also used which is capable of immunologically reacting with the ligand at a site different than the site where the first species react. The result of the method is the formation of a ternary complex of the two distinct immunological species with the ligand. At least one of the immunological species is covalently attached to a core/shell particle described herein which is labeled in the core with a tracer material. In a preferred immunometric assay, both immunological species are distinct antibodies directed against an antigen. They can be the same or different antibodies, whole or fragments, monoclonal or polyclonal.

In still another embodiment of this invention, the reagent of this invention is comprised of an antigen and the ligand to be determined is an antibody. The amount of antibody in the test sample is measured by determining the amount of tracer in the reacted or unreacted materials.

The method of this invention can also be practiced using a dry analytical element. The simplest element can be composed of an absorbent carrier material, for example, a thin sheet of a self-supporting absorbent or bibulous material, such as filter paper or strips, which has one or more zones, at least one zone containing the reagent of this invention. Other zones can be used to contain other useful reagents. Such elements are known in the art as test strips, diagnostic elements, dip sticks or diagnostic agents.

Useful absorbent carrier materials are insoluble and maintain their structural integrity when exposed to water or biological fluids such as whole blood or serum. Useful elements can be prepared from paper, porous particulate structures, porous polymeric films, cellulose, glass fibers, woven and nonwoven fabrics (synthetic and nonsynthetic) and the like. Useful materials and procedures for making such elements are well known in the art.

Preferably, the absorbent carrier material of the dry analytical element of this invention is a porous spreading zone. This zone can be self-supporting (that is, composed of a material rigid enough to maintain its integrity), but preferably it is carried on a separate support. Such a support can be any suitable dimensionally stable, and preferably, nonporous and transparent (that is, radiation transmissive) material which transmits electromagnetic radiation of a wavelength between about 200 and about 900 nm. A support of choice for a particular element should be compatible with the intended mode of detection (fluorescence, transmission or reflectance spectroscopy). Useful supports can be prepared from paper, metal foils, polystyrene, polyesters, polycarbonates or cellulose esters.

The porous spreading zone can be prepared from any suitable fibrous or non-fibrous material or mixtures of either or both. The void volume and average pore size of this zone can be varied depending upon the use intended. UseFul spreading zones can be prepared using materials and procedures described, for example, in U.S. Pat. No. 4,292,272 (issued Sept. 29, 1981 to Kitajima et al), U.S. Pat. No. 3,992,158 (issued Nov. 16, 1976 to Przybylowicz et al), U.S. Pat. No. 4,258,001 (issued Mar. 24, 1981 to Pierce et al) and U.S. Pat. No. 4,430,436 (issued Feb. 7, 1984 to Koyama et al) and Japanese Patent Publication 57(1982)-101760.

The elements can have two or more discrete zones, either in the same layer or superimposed. At least one of the zones is preferably a porous spreading zone. The other zones can be reagent zones or registration zones as those zones are known in the art, additional spreading zones, radiation-blocking or filter zones, subbing zones or barrier zones. The zones are generally in fluid contact with each other, meaning that fluids, reagents and reaction products (for example, color dyes) can pass or be transported between superposed regions of adjacent zones. In other words, when the element is contacted with fluid, the reagents within the element become mixed and can readily interact. Preferably, each zone is a separately coated layer, although two or more zones can be separate areas in a single layer of the element.

Preferably, the reagent of this invention is used to detect a multivalent immunoreactive species, such as Streptococcus A antigen as is demonstrated in the following embodiment and in Example 1 below. This embodiment of the invention relating to Streptococcus A antigen is presented for illustrative purposes, but it will be understood that the scope of this invention is not so limited. A biological sample suspected of containing the antigen can be collected from a patient in any suitable manner. Subsequently, the antigens are extracted from the organisms in a suitable manner. It should be understood that some antigens are determinable directly without extraction procedures.

In the case of Streptococcus A antigen, useful extraction compositions known in the art include a mixture of nitrite salt and glacial acetic acid, as described in E.P. Publication 150,567, and enzymes derived from the bacterium *Streptomyces albus* as described in U.S. Pat. No. 4,618,576, noted above. A preferred extraction composition is a mixture of a nitrite salt (for example, sodium nitrite or potassium nitrite) with an organic acid (for example, succinic or citric acid), as described in copending and commonly assigned U.S. Ser. No. 098,431, filed Sept. 18, 1987 by Snyder et al now abandoned in favor of Continuation-in-part U.S. Ser. No. 131,618 (filed Dec. 11, 1987), now U.S. Pat. No. 4,808,524 (issued Feb. 28, 1989).

The presence of a ligand, for example, Streptococcus A antigen, is detected by the immunoreactive reagent of this invention which can comprise antibody molecules covalently bound to the particles. Reaction (or immunochemical binding) between immunoreactive species and antibodies then results in a reactive product which can be detected by measuring the amount of tracer in the resulting reaction product or in unreacted materials.

Once a reaction product, such as an agglutinate, has been formed, the reaction product is optionally but preferably separated from unagglutinated materials in any suitable manner known in the art. Following separation, the amount of tracer is preferably determined in the agglutinate.

Simultaneously or subsequent to contact of the reagent with receptor molecules to form the agglutinate, the agglutinate can also be contacted with a microporous water-insoluble membrane to effect separation. In one embodiment, the agglutinate can be formed in a separate container and then brought into contact with the membrane Alternatively and preferably, the agglutinate is formed in the presence of the membrane. This membrane (described in detail below) can be simply a filter means held by hand through which unagglutinated materials are filtered. Preferably, however, it is mounted in a test device in which the assay is carried out. Such a test device is also described below.

Any microporous water-insoluble membrane can be used as long as it is inert to the materials used in the assay, and has the desired porosity which will allow fluids and unreacted materials to pass through but which will retain the reaction product. In other words, the membrane pores must be large enough to allow passage of the reagent, and unreacted particles, but not large enough to allow agglutinated particles to pass through. More particularly, the average pore size of the membrane must be at least five times the average diameter of the water-insoluble particles described above. Preferably, the average pore size is from about 6 to about 15 times the average particle diameter. Useful membranes include polymeric materials which are commercially available from various sources, such as Pall Corp (Glen Cove, N.Y.). One useful membrane is a nylon-66 microporous membrane manufactured and marketed by that company as BIODYNE A or ULTIPOR N-66.

In an agglutination assay, a suitable incubation period can be used to optimize agglutination, if desired, before or during contact with the membrane. After that period, unagglutinated residual materials are washed through the membrane while leaving the agglutinate thereon Any suitable wash fluid can be used in this step. Details regarding a preferred wash solution are provided in U.S. Ser. No. 19,850, filed Feb. 27, 1987 by Snyder et al now U.S. Pat. No. 4,847,199 (issued July 11, 1989).

Once the unagglutinated residual materials have been washed through the membrane, the amount of immunoreactive species in either the agglutinate or residual materials can generally be determined with the unaided eye if the tracer is a readily viewable colorimetric compound. Otherwise, standard colorimetric detection equipment can be used. Other types of tracers, for example, radioisotopes, fluorescent dyes, phosphorescent dyes, and the like, require suitable detection equipment.

While the present invention is not so limited, the assay for a multivalent immunoreactive species can be carried out using a suitable test device which comprises the microporous membrane described herein. Such a device can have one or more wells into which a test sample containing a ligand is added for reaction with the reagent of this invention. This reagent can be added to the device during the assay, or incorporated therein at the time of manufacture. Once an agglutinate is formed, the unagglutinated residual materials can be washed through tee membrane with the wash solution into a separate compartment below the membrane. An example of such a test device is described and claimed in copending and commonly assigned U.S. Ser. No. 19,810 filed Feb. 27, 1987 by Hinckley. Other variations of useful test devices would be within the purview of an ordinary worker skilled in the art.

The following examples illustrate the practice of the present invention.

EXAMPLE 1

Preparation of Reagent

This example illustrates the preparation of a core/shell polymer particle, the inclusion of a tracer material and the attachment of an immunological species in the preparation of a reagent of the present invention.

Preparation of Core/Shell Polymeric Particles

The three solutions outlined below were continuously added to a 1300 ml vessel containing deoxygenated water at 80° C. at the indicated rates:

Solution 1: Styrene (103 g), 2-acetoacetoxyethyl methacrylate (91 g) and 1-dodecanethiol (1.9 g) at 1.08 g/min. for 180 minutes.

Solution 2: Ammonium Persulfate (6.5 g) and distilled, deoxygenated water (651 g) at 2.13 g/min. for 300 minutes.

Solution 3: Sodium pyrosulfite (3.24 g) and distilled water (651 g) at 2.17 g/min. for 300 minutes.

After 180 minutes, Solution 1 was exhausted, and replaced with a solution of m and p-chloromethylstyrene (130 g) and 1-dodecanethiol (1.3 g) which was added at a rate of 1.08 g for 120 minutes. The final reactor contents were 11.45% solids. After five days of dialysis, the latex was 8.7% solids, and the average size of the resulting core/shell particles was about 0.34 μm as measured by transmission electron microscopy.

Adding Tracer Material to Particles

Kodak Oil Red O Dye (available from Eastman Kodak Co, Rochester, N.Y.) (2.5 g) was dissolved in acetonitrile (150 g). To a 60 g sample of the dialyzed latex described above was added distilled water (290 g), and the resulting mixture was heated to 70° C. with stirring. To the hot latex solution were added 30 g portions of the dye solution, one portion every 30 minutes, until all had been added. The resulting dispersion was filtered, stripped of residual acetonitrile under reduced pressure, and refiltered to yield 70 g of a 4.82% mixture of nonagglutinated core/shell particles having dye in the cores only. The dye content was determined spectrophotometrically to be 8.9% (based on polymer weight).

Covalent Attachment of Antibody to Particles

Monoclonal antibodies to Streptococcus A antigen and casein were covalently immobilized on these particles as follows: to 0.6 ml of 50 mmolar borate buffer (pH 8.5) was added 0.1 ml of total protein comprised of a 10:1 mixture of anti Strep A antibody (2.9 mg/ml solution in phosphate buffered saline solution, known in the art as PBS) and casein (10 mg/ml water). After mixing, 41.5 μl of a 5% suspension of the polymeric latex particles were added (to provide 0.3% solids) and the resulting solution was rotated (end-over-end) for 24 hours at 37° C. to effect covalent attachment of the antibody and the casein to the particles to form an immunoreactive reagent.

EXAMPLE 2

Determination of Streptococcus A Using Reagent of This Invention

This example demonstrates the use of the reagent of this invention to determine the presence of Streptococcus A antigen in a biological sample.

A solution of succinic anhydride (10 mg/ml dimethyl sulfoxide) was added to a suspension of the reagent prepared in Example 1 above at a weight ratio of 1 part anhydride to 1 part total protein. The resulting suspension was mixed for four hours at 25° C., then centrifuged for 5 minutes at 7000 rpm and the resulting pellet was resuspended in 0.1 molar glycine buffer (pH 8.5) to a concentration of 0.3% solids. This procedure chemically modified the primary and secondary amine groups of the proteins attached to the particles whereby a hydrogen atom on the amine groups is substituted with a carboxylic acid group.

Streptococcus A antigen was extracted from an isolate obtained from a local hospital at 25° C. for minute using a solution of equal volumes of sodium nitrite (8 molar) and citric acid (0.2 molar). The solution was then neutralized with an equal volume of 3-(N-morpholino)-propanesulfonic acid buffer (2 molar, pH 7.5) containing ethylenediaminetetraacetic acid (75 mmolar).

A nylon 66 microporous membrane (5 μm average pore size) was incorporated into a test well of a disposable test device like that described and claimed in U.S. Ser. No. 19810 of Hinckley, noted above, and pretreated by washing with 100 μl of a 2% succinylated casein solution.

A mixture of sodium chloride (80 μl, 1 molar), the reagent suspension described above (40 μl ), and extracted antigen (80 μl) containing about $4.2 \times 10^5$ colony-forming units was added to the test well of the test device containing the membrane, and incubated therein for two minutes at 25° C. The fluid was then allowed to drain into a compartment below the membrane, and the agglutinate on the membrane was washed with 150 μl of a wash fluid having an ionic strength of 0.25.

After the washing step, the amount of dye in the agglutinate on the membrane was measured at 540 nm using reflectance measuring equipment. The Williams-Clapper transform (*J. Optical Soc. Am.*, 43 p. 595, 1953) was used to calculate transmission density values. The agglutinate on the membrane was readily observable and had a significantly greater density value than the density of a background control (the difference was 0.148). These data indicate that the reagent of the present invention was useful for determination of Streptococcus A antigen from a biological sample.

EXAMPLE 3

Determination of hCG Using a Reagent of This Invention

This example demonstrates the practice of the present invention for the determination of human chorionic gonadotropin (hCG).

Core/shell polymeric particles were imbibed with Oil Red EGN dye according to the procedure shown in Example 1 above. The particle cores were composed of poly(styrene-co-2-acetoacetoxyethyl methacrylate) (85:15 weight ratio), and the particle shells were composed of poly(m and p-chloromethylstyrene-co-methacrylic acid) (99.8:0.2 weight ratio). The particles had an average diameter of about 0.32 micrometer.

Monoclonal antibodies to two different epitopic sites of hCG were covalently immobilized on these particles as follows: to 0.6 ml of 50 mmolar borate buffer (pH 8.5) were added 0.1 mg of 10:1 mixture of hCG antibody (2.9 mg/ml phosphate buffered saline solution) and casein (10 mg/ml water). After mixing, 41.5 µl of a 5% suspension of the latex particles described above were added and the resulting suspension was rotated (end-over-end) for 24 hours at 37° C. to effect covalent attachment of the antibodies and casein tot&he particles to form an immunoreactive reagent.

A solution of succinic anhydride (10 mg/ml dimethyl sulfoxide) was added to a mixture of the reagent at a weight ratio of 1 part anhydride to 1 part total protein, and the resulting mixture was mixed for 4 hours at 25° C. and centrifuged for 5 minutes at 7000 rpm in order to chemically modify the amine groups of the attached proteins. The resulting pellet was resuspended in 0.1 molar glycine (pH 8.5) to a concentration of 0.3% solids.

Various amounts of hCG (milli I.U./ml) were added to phosphate buffered saline solutions (0.1 molar sodium phosphate and 0.15 molar sodium chloride) containing 0.5% bovine serum albumin. A nylon 66 microporous membrane having an average pore size of about 5 micrometers was incorporated into a test well of a disposable test device similar to that described in Example 2 above. This membrane was washed with 2 drops of a 1% aqueous solution of succinylated casein. The hCG concentration in milli I.U. is defined as 5000 milli I.U. being equivalent to 1 microgram of purified hCG.

A mixture of 60 µl of 4 molar sodium chloride, 1 molar tricine buffer (pH 8.6), 60 µl of suspension of the immunoreactive reagent described above and 240 µl of the hCG solutions described above was added to test tubes, gently mixed and allowed to incubate at 25° C. for 10 minutes. A portion of each solution (300 µl) was added to the test well containing the membrane and allowed to flow through the membrane. Agglutinate formed on the membrane did not flow through, however. It was washed with 300 µl of a 1 molar sodium chloride solution, and the amount of dye in the agglutinate was measured at 540 nm as described in Example 2. The results of these measurements are shown in Table I below as transmission density ($D_T$). It indicates that the assay of this invention can be used to determine hCG.

TABLE I

| hCG Antigen (milli I.U./ml) | $D_T$ |
|---|---|
| 0 | 0.043 |
| 500 | 0.047 |
| 1000 | 0.133 |

EXAMPLE 4

Agglutination Reagent Using Polymer Derived from A Chloroethylsulfonyl Monomer

Core-shell polymeric latex beads, comprising a core of poly(styrene-co-2-acetoacetoxyethyl methacrylate) (85:15 molar ratio) and a shell of poly[styrene-co-m and p-(2-chloroethylsulfonylmethyl)styrene] (95.5:4.5 molar ratio), were prepared and imbibed with a 3.5% acetonitrile solution of Oil Red EGN dye as described in Example 1. The beads were suspended in 0.05 molar sodium borate buffer (pH 8.5) containing 0.1% sodium azide to provide a 0.3% solid suspension.

Monoclonal antibodies to Strep A [0.026 ml of a 3.8 mg/ml solution in 0.05 molar borate buffer (pH 8.5) containing 0.1% sodium azide] and casein (0.01 ml of a 1 mg/ml solution in water) were mixed together in about 0.9 ml of borate buffer.

The beads (0.173 ml of a 1.73% buffer suspension) were added, and the mixture was mixed end-over-end for 24 hours at about 25° C. Succinic anhydride (0.01 ml of a 10 mg/ml of dimethyl sulfoxide solution) was added, and the mixture was rocked for 3 hours. The mixture was centrifuged, the supernatant decanted, and the pellet was suspended in 0.1 normal glycine (pH 8.5) containing 0.1% sodium azide to provide a 0.3% solid suspension.

EXAMPLE 5

Comparative Example

This example compares the reagent of this invention as prepared in Example 1 to a Control reagent which is composed of a homogeneous polymeric particle. The reagents were compared by using them in assays for Streptococcus A antigen as described in Example 2.

The particles of the Control reagent were composed of poly(styrene-co-m and p-chloromethylstyrene-co-2-hydroxyethyl acrylate) (67:30:3 molar ratio) and had an average particle size of 0.77 µm. Residual monomer, initiator and initiator by products from the preparation of the particles were removed using cross flow filtration. Kodak Oil Red O dye was then incorporated into the particles according to the procedure used in Example 2 above. Anti-Streptococcus A antibody was then covalently attached to the particles as described in Example 2, and the resulting reagent was evaluated as described in Example 3.

It was observed in the Streptococcus A assay that the Control reagent did not agglutinate on the membrane filter to provide a detectable agglutination. The particles did contain active antibody, but it appears that the presence of dye on the particle surface interfered in some manner with the desired immunological reaction. In contrast, the reagent of the present invention agglutinated readily and provided a detectable agglutinate on the filter membrane.

The invention has been described in detail with particular reference to preferred embodiments thereof, but it will be understood that variations and modifications can be effected within the spirit and scope of the invention.

We claim:

1. A water-insoluble polymeric particle having:
    an inner core comprising a detectable tracer distributed within a first polymer for which said tracer has a high affinity and which has a glass transition temperature ($Tg_1$) of less than about 100° C., said first polymer being derived from one or more ethylenically unsaturated polymerizable monomers, and
    an outer shell comprising a second polymer for which said tracer has substantially less affinity relative to said first polymer, said second polymer having a glass transition temperature ($Tg_2$) greater than or equal to the term ($Tg_1 - 10°$ C.), and being derived from one or more ethylenically unsaturated polymerizable monomers, at least one of which monomers has reactive groups which are directly or indirectly reactive with free amino or sulfhydryl groups of an immunoreactive species, provided that said outer shell is swellable in water-miscible organic solvents, wherein said first polymer is represented by the formula (I):

X is from 45 to about 99 mole percent, y is from about 1 to 50 mole percent, and z is from 0 to about 5 mole percent.

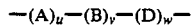
$$-(A)_u-(B)_v-(D)_w-$$

wherein —A— represents recurring units derived from one or more hydrophobic ethylenically unsaturated monomers which provide water insolubility to said particles, —B— represents recurring units derived from one or more ethylenically unsaturated monomers whose homopolymers have a glass transition temperature less than about 55° C., —D— represents recurring units derived from one or more ethylenically unsaturated monomers which are different than those represented by —A— or —B—, u is from about 30 to about 95 mole percent, v is from 5 to about 50 mole percent, and w is from 0 to 20 mole percent, and said second polymer is represented by the formula (II):

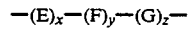
$$-(E)_x-(F)_y-(G)_z-$$

wherein —E— represents recurring units derived from one or more hydrophobic ethylenically unsaturated aromatic monomers, —F— represents recurring units derived from one or more ethylenically unsaturated monomers having reactive groups which will directly or indirectly react with said free amine or sulfhydryl groups of said immunoreactive species, —G— represents recurring units derived from one or more ethylenically unsaturated monomers which are different than those represented by —E— of —F—, x is from 45 to about 99 mole percent, y is from about 1 to 50 mole percent, and z is from 0 to about 5 mole percent, said particle having substantially none of said tracer within said outer shell or on its outer surface, and said particle being covalently attached through said reactive groups on the outer surface to (b) an immunoreactive species which is capable of participating in an immunological reaction with a compound of biological interest.

2. The particle of claim 1 having a diameter of from about 0.05 to about 5 micrometers.

3. The particle of claim 1 wherein said monomers from which said —F— units of said second polymer are derived have reactive groups selected from the group consisting of halomethyl, activated 2-substituted ethylsulfonyl and vinylsulfonyl reactive groups.

4. The particle of claim 1 wherein said monomers represented by D include at least one ethylenically unsaturated polymerizable monomer having anionic groups.

5. The particle of claim 1 wherein said inner core is from about 30 to about 80 percent based on the total polymer particle weight.

6. The particle of claim 1 wherein said detectable tracer is selected from the group consisting of a colorimetric compound, fluorometric compound and a dye-forming compound.

7. The polymeric particle of claim 1 wherein said outer shell is swellable in water-miscible solvents selected from the group consisting of acetonitrile, N,N-dimethylformamide, lower alcohols, tetrahydrofuran, ketones and 1-methyl-2-pyrrolidinone.

8. An immunoreactive reagent comprising:

(a) a water-insoluble polymeric particle having:

an inner core comprising a detectable tracer distributed within a first polymer for which said tracer has a high affinity and having a glass transition temperature ($T_{g1}$) of less than about 100° C., said first polymer being derived from one or more ethylenically unsaturated polymerizable monomers, and an outer shell composed of a second polymer for which said tracer has substantially less affinity relative to said first polymer, said second polymer having a glass transition temperature ($T_{g2}$), greater than or equal to the term ($T_{g1} - 10°$ C.), and being derived from one or more ethylenically unsaturated polymerizable monomers, at least one of which monomers has reactive groups which are directly or indirectly reactive with free amino or sulfhydryl groups of an immunoreactive species, provided that said outer shell is swellable in water-miscible organic solvents, wherein said first polymer is represented by the formula (I):

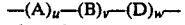
$$-(A)_u-(B)_v-(D)_w-$$

wherein —A— represents recurring units derived from one or more hydrophobic ethylenically unsaturated monomers which provide water insolubility to said particles, —B— represents recurring units derived from one or more ethylenically unsaturated monomers whose homopolymers have a glass transition temperature less than about 55° C., —D— represents recurring units derived from one or more ethylenically unsaturated monomers which are different than those represented by —A— or —B—, u is from about 30 to about 95 mole percent, v is from 5 to about 50 mole percent, and w is from 0 to 20 mole percent, and said second polymer is represented by the formula (II):

$$-(E)_x-(F)_y-(G)_z-$$

wherein —E— represents recurring units derived from one or more hydrophobic ethylenically unsaturated aromatic monomers, —F— represents recurring units derived from one or more ethylenically unsaturated monomers having reactive groups which will directly or indirectly react with said free amine or sulfhydryl groups of said immunoreactive species;

—G— represents recurring units derived from one or more ethylenically unsaturated monomers which are different than those represented by —E— or —F—, x is from 45 to about 99 mole percent, y is from about 1 to 50 mole percent, and z is from 0 to about 5 mole percent, said particle having substantially none of said tracer within said outer shell or on its outer surface, and said particle being covalently attached through said reactive groups on the outer surface to (b) an immunoreactive species which is capable of participating in an immunological reaction with a compound of biological interest.

9. The reagent of claim 8 wherein said immunologically reactive species is a drug, hormone, antibiotic, antibody or other compound having antigenic properties.

10. The reagent of claim 8 wherein said immunologically reactive species is an antibody.

11. The reagent of claim 8 wherein said monomers from which —F— recurring units are derived have reactive groups selected from the group consisting of halomethyl, activated 2-substituted ethylsulfonyl and vinylsulfonyl reactive groups.

12. The reagent of claim 8 wherein said detectable tracer is selected from the group consisting of a colorimetric compound, fluorometric compound and a dye forming compound.

13. An analytical element comprising an absorbent carrier material having one or more zones, and containing in one of said zones an immunoreactive reagent comprising:

(a) a water-insoluble polymeric particle having:

an inner core comprising a detectable tracer distributed within a first polymer for which said tracer has a high affinity and having a glass transition temperature ($Tg_1$) of less than about 100° C., said first polymer being derived from one or more ethylenically unsaturated polymerizable monomers, and an outer shell comprising a second polymer for which said tracer has substantially less affinity relative to said first polymer, said second polymer having a glass transition temperature ($Tg_2$) greater than or equal to the term ($Tg_1 - 10°$ C.), and being derived from one or more ethylenically unsaturated polymerizable monomers, at least one of which monomers has reactive groups which are directly or indirectly reactive with free amino or sulfhydryl groups of an immunoreactive species, provided that said outer shell is swellable in water-miscible organic solvents, wherein said first polymer is represented by the formula (I):

$$-(A)_u-(B)_v-(D)_w-$$

wherein —A— represents recurring units derived from one or more hydrophobic ethylenically unsaturated monomers which provide water insolubility to said particles, —B— represents recurring units derived from one or more ethylenically unsaturated monomers whose homopolymers have a glass transition temperature less than about 55° C., —D— represents recurring units derived from one or more ethylenically unsaturated monomers which are different than those represented by —A— or —B—, u is from about 30 to about 95 mole percent, v is from 5 to about 50 mole percent, and w is from 0 to 20 mole percent, and said second polymer is represented by the formula (II):

$$-(E)_x-(F)_y-(G)_z-$$

wherein —E— represents recurring units derived from one or more hydrophobic ethylenically unsaturated aromatic monomers, —F— represents recurring units derived from one or more ethylenically unsaturated monomers having reactive groups which will directly or indirectly react with said free amine or sulfhydryl groups of said immunoreactive species, —G— represents recurring units derived from one or more ethylenically unsaturated monomers which are different than those represented by —E— or —F—, x is from 45 to about 99 mole percent, y is from about 1 to 50 mole percent, and z is from 0 to about 5 mole percent, x is from 45 to about 99 mole percent, y is from about 1 to 50 mole percent, and z is from 0 to about 5 mole percent, said particle having substantially none of said tracer within said outer shell or on its outer surface, and said particle being covalently attached through said reactive groups on the outer surface to (b) an immunoreactive species which is capable of participating in an immunological reaction with a compound of biological interest.

14. The element of claim 13 wherein said immunoreactive species is an antibody.

15. A method of the determination of a compound of biological interest in an aqueous liquid comprising:

A. contacting said liquid with an immunoreactive reagent comprising:

(a) a water-insoluble polymeric particle having:

an inner core comprising a detectable tracer distributed within a first polymer for which said tracer has a high affinity and having a glass transition temperature ($Tg_1$) of less than about 100° C., said first polymer being derived from one or more ethylenically unsaturated polymerizable monomers, and an outer shell comprising a second polymer for which said tracer has substantially less affinity relative to said first polymer, said second polymer having a glass transition temperature ($Tg_2$) greater than or equal to the term ($Tg_1 - 10°$ C.), and being derived from one or more ethylenically unsaturated polymerizable monomers, at least one of which monomers has reactive groups which are directly or indirectly reactive with free amino or sulfhydryl groups of an immunoreactive species, provided that said outer shell is swellable in water-miscible organic solvents, said particle having substantially none of said tracer within said outer shell or on its outer surface, and said particle being covalently attached through said reactive groups on the outer surface to (b) an immunoreactive species which is capable of participating in an immunological reaction with said compound of biological interest, so as to form an insoluble reaction product of said biological compound and said immunoreactive species, B. determining the amount of tracer either in said reaction product or in unreacted materials.

16. The method of claim 15 wherein said reaction product is separated from said unreacted materials prior to said determination step.

17. The method of claim 15 for the determination of Streptococcus A antigen in a biological sample wherein said immunoreactive species is an antibody to Streptococcus A antigen.

18. The method of claim 15 for the determination of hCG in a biological sample wherein said immunoreactive species is an antibody to hCG.

19. The method of claim 15 for the determination of antibodies against a compound of biological interest selected from the group consisting of HTLV and HIV in a biological sample wherein said immunoreactive species is selected from the group consisting of a HTLV and a HIV antigen, respectively.

20. The method of claim 15 wherein, prior to, simultaneously with or subsequent to said contacting step A, contacting said biological compound with a second immunoreactive species which is capable of participating in a specific binding reaction with said compound but which is not reactive with said immunoreactive species of said reagent.

21. An agglutination method for the determination of Streptococcus A antigen in an aqueous liquid comprising:

A. contacting an extraction solution of Streptococcus A organisms with an immunoreactive reagent comprising:
(a) a water-insoluble polymeric particle having:
an inner core comprising a detectable tracer distributed within a first polymer for which said tracer has a high affinity and having a glass transition temperature ($Tg_1$) of less than about 100° C., said first polymer being derived from one or more ethylenically unsaturated polymerizable monomers, and
an outer shell composed of a second polymer for which said tracer has substantially less affinity relative to said first polymer, said second polymer having a glass transition temperature ($Tg_2$) greater than or equal to the term ($Tg_1 - 10°$ C.), and being derived from one or more ethylenically unsaturated polymerizable monomers, at least one of which monomers has reactive groups selected from the group consisting of active halogen atoms, carboxyl, epoxy, isocyanate, amine, aziridine, 2-substituted ethylcarbonyl, aldehyde, activated 2-substituted ethylsulfonyl and vinylsulfonyl, provided that said outer shell is swellable in water-miscible organic solvents,
wherein said first polymer is represented by the formula (I):

$$-(A)_u-(B)_v-(D)_w-$$

wherein —A— represents recurring units derived from one or more hydrophobic ethylenically unsaturated monomers which provide water insolubility to said particles,
—B— represents recurring units derived from one or more ethylenically unsaturated monomers whose homopolymers have a glass transition temperature less than about 55° C.,
—D— represents recurring units derived from one or more ethylenically unsaturated monomers which are different than those represented by —A— or —B—, u is from about 30 to about 95 mole percent, v is from 5 to about 50 mole percent, and w is from 0 to 20 mole percent,
and said second polymer is represented by the formula (II):

$$-(E)_x-(F)_y-(G)_z-$$

wherein —E— represents recurring units derived from one or more hydrophobic ethylenically unsaturated aromatic monomers,
—F— represents recurring units derived from one or more ethylenically unsaturated monomers having reactive groups which will,
said particle having substantially none of said tracer within said outer shell or on its outer surface, and said particle being covalently attached through said reactive groups on the outer surface to
(b) an antibody to Streptococcus A antigen, product of said antigen and said antibody,
B. determining the amount of tracer either in said agglutinate or in unagglutinated materials.

22. An aqueous suspension of a water-insoluble polymeric particle having:
an inner core comprising a detectable tracer distributed within a first polymer for which said tracer has a high affinity and having a glass transition temperature ($Tg_1$) of less than about 100° C., said first polymer being derived from one or more ethylenically unsaturated polymerizable monomers, and
an outer shell comprising a second polymer for which said tracer has substantially less affinity relative to said first polymer, said second polymer having a glass temperature ($Tg_2$) greater than or equal to the term ($Tg_1 - 10°$ C.), and being derived from one or more ethylenically unsaturated polymerizable monomers, at least one of which monomers has reactive groups which are directly or indirectly reactive with free amino or sulfhydryl groups of an immunoreactive species, provided that said outer shell is swellable in water-miscible organic solvents,
wherein said first polymer is represented by the formula (I):

$$-(A)_u-(B)_v-(D)_w-$$

wherein —A— represents recurring units derived from one or more hydrophobic ethylenically unsaturated monomers which provide water insolubility to said particles,
—B— represents recurring units derived from one or more ethylenically unsaturated monomers whose homopolymers have a glass transition temperature less than about 55° C.,
—D— represents recurring units derived from one or more ethylenically unsaturated monomers which are different than those represented by —A— or —B—,
u is from about 30 to about 95 mole percent, v is from 5 to about 50 mole percent, and w is from 0 to 20 mole percent,
and said second polymer is represented by the formula (II):

$$-(E)_x-(F)_y-(G)_z-$$

wherein —E— represents recurring units derived from one or more hydrophobic ethylenically unsaturated aromatic monomers, —F— represents recurring units derived from one or more ethylenically unsaturated monomers having reactive groups which will directly or indirectly react with said free amine or sulhydryl groups of said immunoreactive species, —G— represents recurring units derived from one or more ethylenically unsaturated monomers which are different than those represented by —E— or —F—, x is from 45 to about 99 mole percent, y is from about 1 to 50 mole percent, and z is from 0 to about 5 mole percent.

23. An aqueous suspension of an immunoreactive reagent comprising:
(a) a water-insoluble polymeric particle having:
an inner core comprising a detectable tracer distributed within a first polymer for which said tracer has a high affinity and having a glass transition temperature ($Tg_1$) of less than about 100° C., said first polymer being derived from one or more ethylenically unsaturated polymerizable monomers, and
an outer shell composed of a second polymer for which said tracer has substantially less affinity relative to said first polymer, said second polymer having a glass transition temperature ($Tg_2$) greater than or equal to the term ($Tg_1 - 10°$ C.), and being derived from one or more ethylenically unsaturated polymerizable monomers, at least one of which monomers has reactive groups which are directly or indirectly reactive with free amino or sulfhydryl groups of an immunoreactive species, provided that said outer shell is swellable in water-miscible organic solvents,
wherein said first polymer is represented by the formula (I):

$$-(A)_u-(B)_v-(D)_w-$$

wherein —A— represents recurring units derived from one or more hydrophobic ethylenically unsaturated monomers which provide water insolubility to said particles, —B— represents recurring units derived from one or more ethylenically unsaturated monomers whose homopolymers have a glass transition temperature less than about 55° C., —D— represents recurring units derived from one or more ethylenically unsaturated monomers which are different than those represented by —A— or —B—, u is from about 30 to about 95 mole percent, v is from 5 to about 50 mole percent, and w is from 0 to 20 percent, and said second polymer is represented by the formula (II):

$$-(E)_x-(F)_y-(G)_z-$$

wherein —E— represents recurring units derived from one or more hydrophobic ethylenically unsaturated aromatic monomers, —F— represents recurring units derived from one or more ethylenically unsaturated monomers having reactive groups which will directly or indirectly react with said free amine or sulfhydryl groups of said immunoreactive species, —G— represents recurring units derived from one or more ethylenically unsaturated monomers which are different than those represented by —E— or —F—, tracer has a high affinity and which has a x is from 45 to 99 mole percent, y is from about 1 to 50 mole percent, and z is from 0 to about 5 mole percent directly or indirectly react with said free amine or sulfhydryl groups of said immunoreactive species, —G— represents recurring units derived from one or more ethylenically unsaturated monomers which are different than those represented by —E— or —F—, x is from 45 to about 99 mole percent, y is from about 1 to 50 mole percent, and z is from 0 to about 5 mole percent, said particle having substantially none of said tracer within said outer shell or on its outer surface, and said particle being covalently attached through said reactive groups on the outer surface to (b) an immunoreactive species which is capable of participating in an immunological reaction with a compound of biological interest.

* * * * *

UNITED STATES PATENT AND TRADEMARK OFFICE
CERTIFICATE OF CORRECTION

Page 1 of 3

PATENT NO. : 4,997,772

DATED : March 5, 1991

INVENTOR(S) : Richard C. Sutton et al

It is certified that error appears in the above-identified patent and that said Letters Patent is hereby corrected as shown below:

Col. 21, lines 3-5 should be deleted.

Column 21, lines 46-52 should be deleted.

Column 21, line 45, delete "," and insert --.--.

Column 24, lines 16-18 should be deleted.

Column 24, line 52, after vents, the following additional material is shown on attached sheet.

--wherein said first polymer is represented by the formula (I):

$$--(A)_u--(B)_v--(D)_w--$$

wherein —A— represents recurring units derived from one or more hydrophobic ethylenically unsaturated monomers which provide water insolubility to said particles, —B— represents recurring units derived from one or more ethylenically unsaturated monomers whose homopolymers have a glass transition temperature less than about 55°C,

UNITED STATES PATENT AND TRADEMARK OFFICE
CERTIFICATE OF CORRECTION

PATENT NO. : 4,997,772
DATED : March 5, 1991
INVENTOR(S) : Richard C. Sutton, et al It is certified that error appears in the above-identified patent and that said Letters Patent is hereby corrected as shown below:

—D— represents recurring units derived from one or more ethylenically unsaturated monomers which are different than those represented by —A— or —B—, u is from about 30 to about 95 mole percent, v is from 5 to about 50 mole percent, and w is from 0 to 20 mole percent, and said second polymer is represented by the formula (II):

wherein —E— represents recurring units derived from one or more hydrophobic ethylenically unsaturated aromatic monomers, —F— represents recurring units derived from one or more ethylenically unsaturated monomers having reactive groups which will directly or indirectly react with said free amine or sulfhydryl groups of said immunoreactive species,

UNITED STATES PATENT AND TRADEMARK OFFICE
CERTIFICATE OF CORRECTION

PATENT NO. : 4,997,772
DATED : March 5, 1991
INVENTOR(S) : Richard C. Sutton et al It is certified that error appears in the above-identified patent and that said Letters Patent is hereby corrected as shown below:

-G- represents recurring units derived from one or more ethylenically unsaturated monomers which are different than those represented by -E- or -F-, x is from 45 to about 99 mole percent, y is from about 1 to 50 mole percent, and z is from 0 to about 5 mole percent--

Column 26, line 15, after will, should read: --directly or indirectly react with said free amine or sulfhydryl groups of said immunoreactive species,
-G- represents recurring units derived from one or more ethylenically unsaturated monomers which are different than those represented by -E- or -F-,
x is from 45 to about 99 mole percent, y is from about 1 to 50 mole percent, and z is from 0 to about 5 mole percent--

Column 28, line 30, starting with "tracer" through to line 39, should be deleted.

Signed and Sealed this

Third Day of August, 1993

Attest:

MICHAEL K. KIRK

*Attesting Officer*   *Acting Commissioner of Patents and Trademarks*